(12) United States Patent
Jakobsen et al.

(10) Patent No.: US 12,310,984 B1
(45) Date of Patent: *May 27, 2025

(54) COMPOSITION AND METHOD FOR REDUCING RISK OF HYPOCALCEMIA IN PERIPARTURIENT RUMINANT ANIMALS

(71) Applicant: Protekta Inc., Lucknow (CA)

(72) Inventors: Morten Jakobsen, Lucknow (CA); Lasse Jakobsen, Newport Beach, CA (US); Rod Martin, Brooklyn, WI (US); Meghan Connelly, Rochester, MN (US); Patrick Hoffman, Spencer, WI (US)

(73) Assignee: Protekta Inc., Lucknow (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/830,440

(22) Filed: Sep. 10, 2024

Related U.S. Application Data

(63) Continuation-in-part of application No. 18/618,702, filed on Mar. 27, 2024.

(60) Provisional application No. 63/601,401, filed on Nov. 21, 2023.

(51) Int. Cl.
| | | |
|---|---|---|
| *A61K 9/00* | (2006.01) | |
| *A61K 33/06* | (2006.01) | |
| *A61P 3/02* | (2006.01) | |

(52) U.S. Cl.
CPC ............ *A61K 33/06* (2013.01); *A61K 9/0053* (2013.01); *A61P 3/02* (2018.01)

(58) Field of Classification Search
None
See application file for complete search history.

(56) References Cited

U.S. PATENT DOCUMENTS

| | | | |
|---|---|---|---|
| 4,931,290 A | 6/1990 | Rebhan | |
| 5,840,853 A | 11/1998 | Segre et al. | |
| 6,890,550 B1 | 5/2005 | Jorgensen | |
| 7,235,256 B2 | 6/2007 | Jorgensen | |
| 8,034,833 B2 * | 10/2011 | Nelson | A23L 33/175 |
| | | | 514/375 |
| 8,999,169 B2 | 4/2015 | Gotch et al. | |
| 10,220,047 B2 | 3/2019 | Petkovich et al. | |
| 2005/0147695 A1 | 7/2005 | Jorgensen | |
| 2005/0261256 A1 | 11/2005 | Delgado-Herrera et al. | |
| 2010/0135950 A1 | 6/2010 | Huval | |
| 2012/0195964 A1 | 8/2012 | Lewis et al. | |
| 2019/0345600 A1 * | 11/2019 | Koh | A61L 15/44 |
| 2020/0281881 A1 | 9/2020 | Hull, Jr. et al. | |

FOREIGN PATENT DOCUMENTS

| | | | | |
|---|---|---|---|---|
| AU | 2010309784 A1 * | 5/2012 | ............. | A61K 33/10 |
| CN | 101595131 A * | 12/2009 | ............. | A61P 13/02 |
| CN | 105010829 | 11/2015 | | |
| DE | 10231104 | 1/2004 | | |
| JP | 2009022258 | 2/2009 | | |
| WO | WO-2010117370 A1 * | 10/2010 | ............. | A61K 31/19 |
| WO | 2024/125758 | 6/2024 | | |

OTHER PUBLICATIONS

Cohrs et al. (Short Communication: Effect of dietary phosphorus deprivation in late gestation and early lactation on the calcium homeostasis of periparturient dairy cows); J. Dairy Sci. 101-9591-9598. (Year: 2018).*
Grunberg et al. J Vet Intern Med (Year: 2005), "Phosphorus Homeostasis in Dairy Cows with Abomasal Displacement or Abomasal Volvulus".*
Cohrs et al. Effect of dietary phosphorus deprivation in late gestation and early lactation on the calcium homeostasis of periparturient dairy cows. Journal of Dairy Science, vol. 101, pp. 9591-9598 (Year: 2018).*
Venjakob et al. "Hypocalcemia-Cow level prevalence and preventive strategies in German dairy herds", J. Dairy Sci. 100:9258-9266. (Year: 2017).*
Cohrs et al. "Effect of dietary phosphorus deprivation in late gestation and early lactation on the calcium homeostasis of periparturient dairy cows", J. Dairy Sci. 101:9591-9598. (Year: 2018).*
Thilsing-Hansen et al. "Prevention of Parturient Paresis and Subclinical Hypocalcemia in Dairy Cows by Zeolite A Administration in the Dry Period", J. Dairy Sci. 84:691-693. (Year: 2001).*
Cohrs et al., Short communication: Effect of dietary phosphorus deprivation in late gestation and early lactation on the calcium homeostasis of periparturient dairy cows, Journal of Diary Science, vol. 101, No. 10, Published 2018.

(Continued)

*Primary Examiner* — Susan T Tran

(74) *Attorney, Agent, or Firm* — Concourse Law Group; Katherine B. Sales, Esq.

(57) ABSTRACT

A method of reducing risk of periparturient hypocalcemia in a periparturient ruminant animal involves: measuring blood phosphorus concentration in the animal; and, administering a composition containing a phosphorus-binding compound and optionally, a pharmacologically acceptable carrier to the animal during at least part of a prepartum period of the animal, the composition having an effective amount of the phosphorus-binding compound to control the blood phosphorus concentration in a range of 1.5-3.5 mg P per dL of blood in the animal.

6 Claims, 2 Drawing Sheets

(56) References Cited

OTHER PUBLICATIONS

Figure 1:
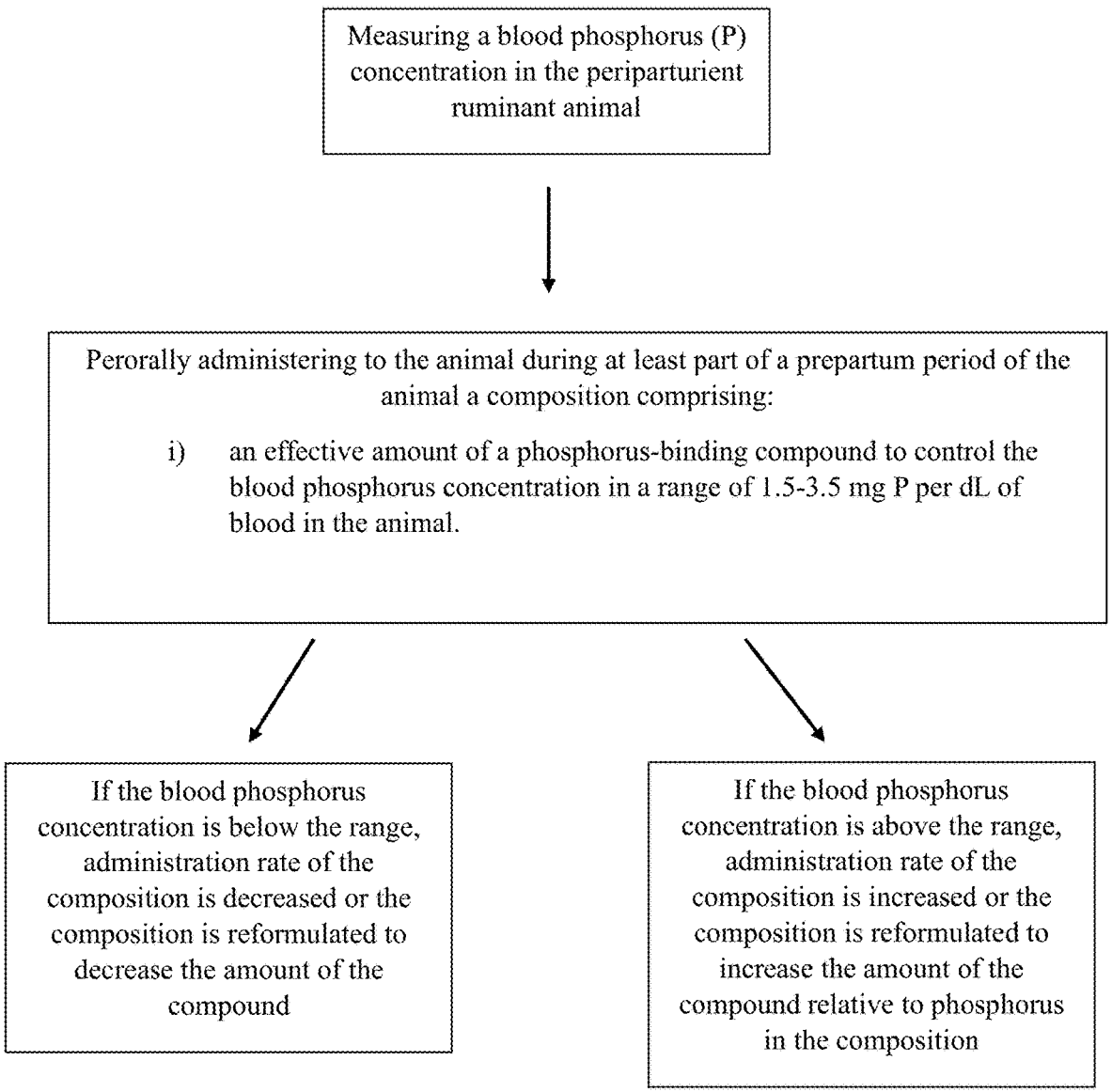

Nakhoul et al., Hyperphosphatemia in Kidney Disease: How to Choose a Phosphorus Binder, Consult QD, published Jan. 9, 2019 https://consultqd.clevelandclinic.org/hyperphosphatemia-in-kidney-disease-how-to-choose-a-phosphorus-binder.

Pallesen et al: "Effect of pre-calving zeolite, magnesium and phosphorus supplementation on periparturient serum mineral concentrations", Veterinary Journal, Bailliere Tindall, London, GB, vol. 175, No. 2, Feb. 1, 2008 (Feb. 1, 2008), pp. 234-239, XP022491628, ISSN: 1090-0233, DOI: 10.1016/J.TVJL.2007.01.007.

* cited by examiner

COMPOSITION AND METHOD FOR REDUCING RISK OF HYPOCALCEMIA IN PERIPARTURIENT RUMINANT ANIMALS

CROSS-REFERENCE TO RELATED APPLICATIONS

This United States Non-Provisional Patent Application is a continuation-in-part of U.S. Non-Provisional application Ser. No. 18/618,702, titled "COMPOSITION AND METHOD FOR REDUCING RISK OF HYPOCALCEMIA IN PERIPARTURIENT RUMINANT ANIMALS," filed Mar. 27, 2024, which claims priority to U.S. Provisional Application Ser. No. 63/601,401, titled "COMPOSITION AND METHOD FOR REDUCING RISK OF HYPOCALCEMIA IN PERIPARTURIENT RUMINANT ANIMALS," filed Nov. 21, 2023, the contents of which are incorporated by reference herein in their entirety.

FIELD

This application relates to preventing or treating hypocalcemia in periparturient ruminant animals.

BACKGROUND

Milk fever (hypocalcemia) in dairy cows (and other lactating animals) is a metabolic disorder that occurs around calving time. Severe, clinical cases are characterized by very low blood calcium resulting in down and non-responsive cows. Milk fever can be classified as Clinical Hypocalcemia (blood calcium less than 7.0 mg/dl) or Subclinical Hypocalcemia (blood calcium between 7.0-8.5 mg/dl). Clinical hypocalcemia (CH) affects 3-6% of all $2^{nd}$ lactation and older cows. Subclinical hypocalcemia affects 60-80% of $2^{nd}$ lactation and older cows. Subclinical hypocalcemia (SCH) may not present with physical symptoms but the borderline low blood calcium levels during the first 4 days post-calving have been shown to be a significant risk for metabolic diseases. Research shows that cows experiencing SCH have a higher risk for ketosis, retained fetal membranes, metritis, displaced abomasum and mastitis compared to normal blood calcium levels (>8.5 mg/dl). Even though SCH symptoms are not as severe as CH, the fact that it affects a very high percent of periparturient cows, and still presents a health risk suggests that SCH may be just as costly, if not more, to a dairy herd than CH.

Hypocalcemia is caused by the high calcium demand at calving for colostrum synthesis. Colostrum milk has twice the calcium concentration compared to regular milk. When colostrum synthesis is initiated, the periparturient cow's homeostatic mechanism cannot maintain normal blood calcium levels, which is especially true for $2^{nd}$ lactation and older dairy cows. Periparturient cows are in negative calcium balance having 8-9 grams of bodily calcium available but requiring up to 30 grams of calcium daily for colostrum synthesis. The calcium deficit needs to be sourced from the bone to maintain normal blood calcium levels and maintain cow health. Research has focused on trying to elucidate the metabolic reasons for the cow's inability to maintain blood calcium levels.

Dietary mineral binders, such as calcium binders are a known strategy in feeding the periparturient cows. By binding a mineral, such as dietary calcium, an actual calcium deficiency is elicited resulting in the stimulation of the parathyroid hormone and vitamin D activation, which allows the cow to better respond to the blood calcium demand at calving. In essence, calcium binders ensure that the blood homeostatic mechanism is working efficiently at calving time when it is needed most. Additionally, binding minerals beyond calcium can be done, with feeding a phosphorus binder being a relatively new strategy being utilized in the industry. Through binding phosphorus, with the use of an aluminum-based product, a reduction in blood phosphorus occurs stimulating the homeostatic mechanisms needed by the periparturient cow at calving to respond to the calcium demand challenge. This product is fed, but optimizing the rate at which to feed and amount of dietary phosphorus to bind in relation to aluminum can provide challenge.

Further, the ratios of dietary phosphorus to aluminum in total mixed rations (TMR) used in feeding schedules on dairy farms around the United States are inconsistent, varying considerably from farm to farm when these aluminum-based products which bind phosphorus are fed. There is therefore a lack of precision in P:Al ratios in the feeds being used. Thus, there is a need for a method in which the P:Al ratio can be consciously adjusted with a view to maintaining blood phosphorus concentration within a desired level to help reduce the risk of periparturient hypocalcemia in dairy cows.

Thus, there remains a need for effective strategies for reducing the risk of hypocalcemia in periparturient ruminant animals, especially cows.

SUMMARY

The present invention overcomes several of the deficiencies, disadvantages and undesired parameters associated with the known methods and compositions for reducing the risk of periparturient hypocalcemia in periparturient ruminant animals.

In one embodiment, the present invention is directed to a method of reducing risk of periparturient hypocalcemia in a periparturient ruminant animal. The method comprises the steps of a) measuring blood phosphorus (P) concentration in the animal; and, b) administering the composition comprising a phosphorus-binding compound and, optionally, a pharmacologically acceptable carrier to the animal during at least part of a prepartum period of the animal. The composition comprises an effective amount of the phosphorus-binding compound to control the blood phosphorus concentration in a range of 1.5-3.5 mg P per dL of blood in the periparturient ruminant animal.

In a second embodiment, the present invention is directed to a composition for reducing risk of periparturient hypocalcemia in a periparturient ruminant animal. The composition comprises a phosphorus-binding compound present in an amount that controls blood phosphorus concentration in the periparturient ruminant animal in a range of 1.5-3.5 mg P per dL of blood; and, optionally, a pharmacologically acceptable carrier.

Optionally, the blood phosphorus concentration of step a) is controlled to be in a range of 1.8-3.0 mg P per dL of blood.

Optionally, the blood phosphorus concentration of step a) is controlled to be in a range of 2.0-2.5 mg P per dL of blood.

If the blood phosphorus concentration is below the range, administration rate of the composition of step b) is decreased or the composition is reformulated to decrease the amount of the compound and/or increase the phosphorus to aluminum ratio, so that the blood phosphorous concentration is brought into the range.

If the blood phosphorus concentration is above the range, administration rate of the composition of step b) is increased or the composition is reformulated to increase the amount of the compound relative to phosphorus in the composition and/or decrease the phosphorus to aluminum ratio, so that the blood phosphorus concentration is brought into the range.

Optionally, the measuring of the blood phosphorus level is done periodically.

Preferably, the phosphorus-binding compound of the composition reduces bioavailability of the phosphorus in a digestive system of the periparturient ruminant animal.

Optionally, the periparturient ruminant animal is a dairy cow.

Optionally, the composition is a feed composition, and the pharmacologically acceptable carrier comprises one or more animal feed components other than the phosphorus-binding compound.

Optionally, the phosphorus-binding compound comprises an aluminum compound.

Optionally, the feed composition provides a dietary phosphorus (P) to aluminum (Al) weight ratio in a range of 0.7:1 to 1.4:1.

Optionally, the weight ratio of dietary phosphorous to aluminum is in a range of 0.8:1 to 1.1:1.

Optionally, the aluminum compound comprises an aluminosilicate, aluminum sulfate, aluminum chloride, aluminum ammonium sulfate, aluminum potassium sulfate, aluminum sodium sulfate, aluminum calcium silicate, aluminum hydroxide, aluminum bromide, aluminum iodide, aluminum nitrate, aluminum carbonate, a hydrate thereof or any mixture thereof.

Optionally, the aluminum compound comprises aluminum sulfate, aluminum chloride, aluminum hydroxide, a hydrate thereof or any mixture thereof.

DRAWINGS

These and other features, aspects, and advantages of the present invention will become better understood with regard to the following description, appended claims, and accompanying drawings.

Figure 2:
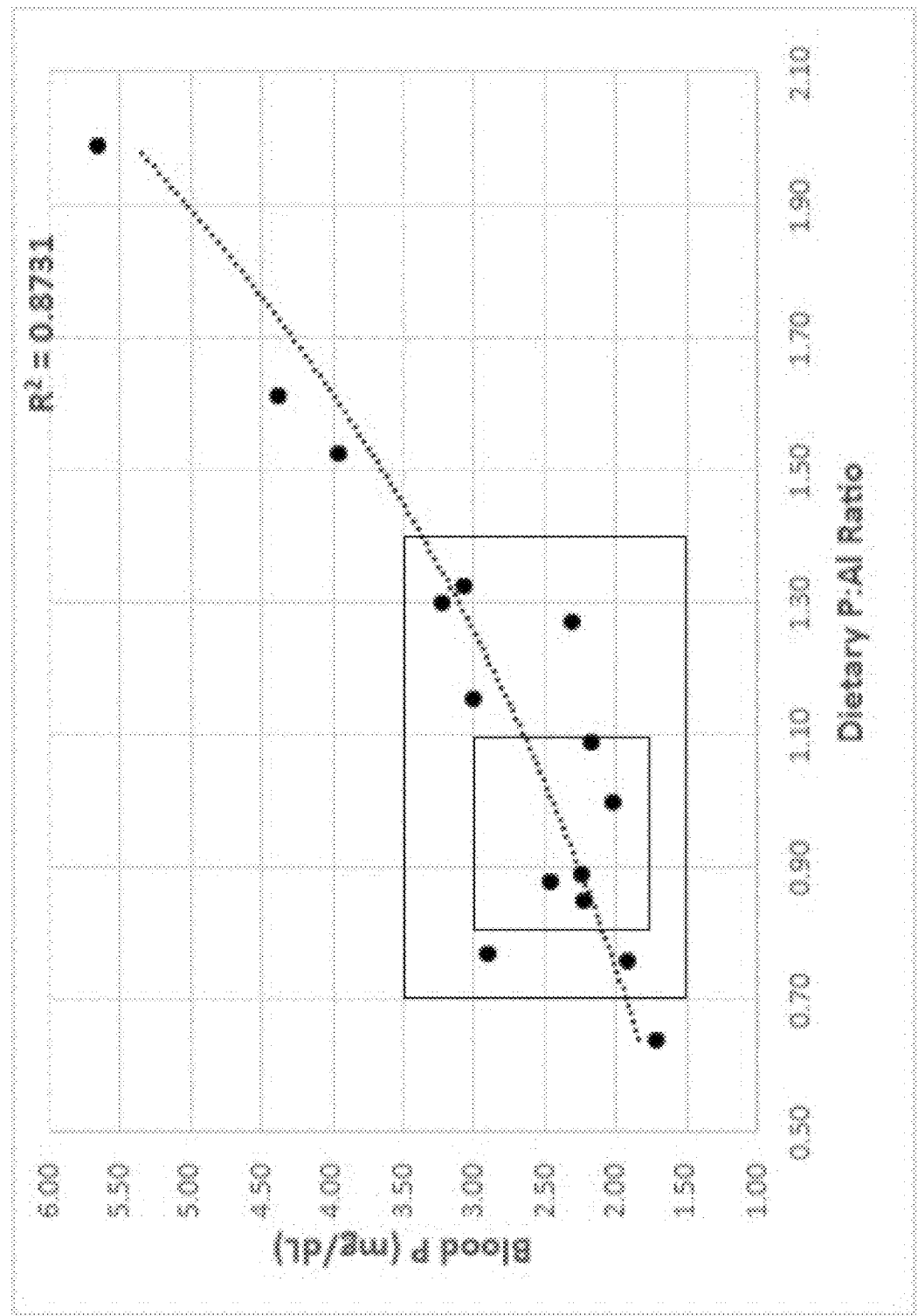

FIG. 1 depicts a flow chart of a method of reducing risk of periparturient hypocalcemia in a periparturient ruminant animal, having features of the present invention; and FIG. 2 depicts a graph showing relationship between blood phosphorus (P) (mg/dL) and dietary P:Al ratio (w/w) discussed in Example 1.

DESCRIPTION

As used herein, the following terms and variations thereof have the meanings given below, unless a different meaning is clearly intended by the contest in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

The term "parturition" refers to the time during which an animal gives birth to an offspring.

The term "prepartum" refers to the time before an animal gives birth to an offspring.

The term "postpartum" refers to the time after an animal gives birth to an offspring.

The term "periparturient" refers to the period of time of parturition and those events within a few weeks prior to and following parturition.

Referring now to FIG. 1, there is shown a flow chart of a method of reducing risk of periparturient hypocalcemia in a periparturient ruminant animal.

There is a strong correlation between blood phosphorus levels and blood calcium levels. Therefore, that concentration of phosphorus in the blood of a periparturient ruminant animal relates to the risk of hypocalcemia. It is also therefore thought that the amount of phosphorus in animal feed has an effect on the incidence of hypocalcemia in periparturient ruminant animals. By reducing bioavailability of phosphorus in the digestive system, especially the small intestine, of the animal during at least part of a prepartum period of the animal, it is possible to reduce the risk of periparturient hypocalcemia in the animal. Reduction of phosphorus bioavailability in the digestive system is preferably accomplished with dietary phosphorus binding using a phosphorus-binding compound.

The phosphorus-binding compounds form complexes or compounds with dietary and gastro-intestinal phosphorus, thereby reducing absorbability of the phosphorus. The phosphorus-binding compounds are therefore particularly useful for reducing the risk of periparturient hypocalcemia in the animal, whether the compound is administered independently of animal feed rations or as a component of animal feed rations.

The phosphorus-binding compound preferably has a binding capacity for phosphorus of at least 60 mg of phosphorus per gram of phosphorus-bonding compound, more preferably at least 65 mg of phosphorus per gram of phosphorus-binding compound.

The binding capacity may be in a range of 60-130 mg of phosphorus per gram of phosphorus-binding compound. Certain pharmacologically acceptable aluminum compounds have been found to be very effective as phosphorus-binding compounds. In some embodiments, the aluminum compound comprises an aluminosilicate (e.g., a zeolite), aluminum sulfate, aluminum chloride, aluminum ammonium sulfate, aluminum potassium sulfate, aluminum sodium sulfate, aluminum calcium silicate, aluminum hydroxide, aluminum bromide, aluminum iodide, aluminum nitrate, aluminum carbonate, a hydrate thereof or any mixture thereof. The aluminum compound preferably comprises aluminum sulfate, aluminum chloride, aluminum hydroxide, a hydrate thereof or any mixture thereof, for example aluminum sulfate, aluminum hydroxide, a hydrate thereof or any mixture thereof. In some embodiments, the aluminum compound is not an aluminosilicate.

The phosphorus-binding compound is used in a pharmacologically acceptable amount that is effective for reducing absorption in the animal of phosphorus from drinking water and/or feed rations. In some embodiments, the phosphorus-binding compound is used in feed composition, for example a total mixed ration (TMR). In some embodiments, the phosphorus-binding comprises an aluminum compound and the amount of aluminum compound used in the feed composition provides a dietary phosphorus (P) to aluminum (Al) weight ratio in a range of 0.7:1 to 1.4:1. In some embodiments, the weight ratio is 0.8:1 to 1.2:1. In some embodiments, the weight ratio is 0.8:1 to 1.1:1. In some embodiments, the weight ratio is 0.9:1 to 1.1:1.

Reducing the risk of hypocalcemia is most effective when blood phosphorus (P) concentration in the animal is kept within a specific range. In some embodiments, the blood phosphorus concentration in the animal is controlled in a range of 1.5-3.5 mg P per dL of blood. In some embodiments, the blood phosphorus concentration is in a range of 1.8-3.3 mg P per dL of blood. In some embodiments, the blood phosphorus concentration is in a range of 1.8-3.0 mg P per dL of blood. In some embodiments, the blood phosphorus concentration is in a range of 2.0-3.0 mg P per dL of blood. In some embodiments, the blood phosphorus concentration is in a range of 2.0-2.5 mg P per dL of blood. In some embodiments, the phosphorus-binding compound is used in a ratio of P:Al in a range of 0.7:1 to 1.4:1 w/w to control blood phosphorus concentration in a range of 1.5-3.5 mg P per dL of blood in the animal. Stated another way, in a pre-fresh cow, the blood phosphorous concentration is in a range of 2.0-3.0 mg/dL. In a fresh cow (preferably, less than 6 hours after calving), the blood phosphorous concentration is in a range of 1.8-3.0 mg/dL. In a post-fresh cow (preferably, greater than 2 days after calving), the blood phosphorous concentration is in a range of 3.5-6.0 mg/dL.

Keeping the blood phosphorus concentration within these ranges has the positive profoundest effect on reducing the risk of hypocalcemia. For this reason, measuring the blood phosphorus concentration is useful. Measurement of blood phosphorus concentration is performed by known methods. In some embodiments, the measurement is done periodically over a period of time, for example once or twice or more per week. In some embodiments, the measurement of blood phosphorus concentration involves taking a blood sample from the animal.

If the blood phosphorus concentration is below the desired range, administration rate of the composition may be decreased, or the composition may be reformulated to decrease the amount of the phosphorus-binding compound relative to phosphorus in the composition. If the blood phosphorus concentration is above the desired range, administration rate of the composition may be increased, or the composition may be reformulated to increase the amount of the phosphorus-binding compound relative to phosphorus in the composition. Either way, the blood phosphorus concentration is desirably brought into the desired range.

The phosphorus-binding compound or composition comprising the phosphorus-binding compound is preferably formulated for peroral administration. The composition may be formulated with just the phosphorus-binding compound, or with a pharmacologically acceptable carrier.

Accordingly, the method of present invention is directed to a method of reducing risk of periparturient hypocalcemia in a periparturient ruminant animal. The method comprises the steps of a) measuring a blood phosphorus (P) concentration in the periparturient ruminant animal; and b) administering to the periparturient ruminant animal during at least part of a prepartum period of the periparturient ruminant animal a composition. The composition comprises an effective amount of a phosphorus-binding compound to control the blood phosphorus concentration in a range of 1.5-3.5 mg P per dL of blood in the periparturient ruminant animal; and, optionally, a pharmacologically acceptable carrier.

If the blood phosphorus concentration is below the range, administration rate of the composition of step b) is decreased or the composition is reformulated to decrease the amount of the compound and/or increase the phosphorus to aluminum ratio.

If the blood phosphorus concentration is above the range, administration rate of the composition of step b) is increased or the composition is reformulated to increase the amount of the compound relative to phosphorus in the composition and/or decrease the phosphorous to aluminum ratio.

Optionally, the measurement of blood phosphorous concentration that is used to adjust the administration of the composition or reformulate the composition is an average blood phosphorous concentration taken across a plurality of animals.

In some embodiments, the composition may be formulated as perorally administrable solution, preferably aqueous solution, or as a dry formulation (e.g., a powder, a tablet, a capsule or the like) and administered separately or coincidentally with feed rations.

Preferably, the composition is a feed composition, e.g., total mixed ration (TMR), in which the phosphorus-binding compound is formulated together with one or more animal feed components other than the phosphorus-binding compound. The one or more other animal feed components is the pharmacologically acceptable carrier and may include, for example, one or more of hay, plant protein products (e.g. soy protein, corn gluten feed (CGF)), grain products (e.g. barley, rye, oats, wheat straw, and the like), processed grain byproducts (e.g. grain silage), processed corn byproducts (e.g. corn silage, corn starch), molasses (e.g. condensed molasses, isomaltulose), fatty acids (e.g. conjugated linoleic acid (CLA)), mineral supplements (e.g. calcium carbonate, monocalcium phosphate, sodium chloride, magnesium oxide, copper sulfate, calcium sulfate, manganese sulfate, zinc sulfate, potassium chloride, potassium sulfate, magnesium sulfate, cobalt carbonate, sodium selenite, magnesium (mica)), vitamin supplements (e.g. Vitamin E, D3-activated animal sterol (a source of vitamin D3), vitamin A), ethylenediamine dihydroiodide, metal-amino acid complexes (e.g. zinc amino acid complex, manganese amino acid complex, copper amino acid complex), mineral oil, preservatives (e.g. propionic acid), brewers' dried yeast, plant extracts (e.g. *yucca schidigera* extract, fenugreek flavor extract, hemicellulose extract), betaine hydrochloride, lactic acid, dried whey, beneficial bacteria (e.g. dried *Bacillus subtilis* fermentation product, dried *Bifidobacterium longum* fermentation product, dried *Bifidobacterium thermophilum* fermentation product, dried *Enterococcus faecium* fermentation product, dried *Lactobacillus acidophilus* fermentation product), dried seaweed meal (e.g. Fucaceae, Bangliceae, Ulvaceae), *psyllium* seed husk, chicory root, red pepper, plant oils (e.g. glycerin, soybean oil, anise oil, *origanum* oil, lemongrass oil), cloves, natural flavor and silicon dioxide, among others.

In feed compositions, the phosphorus-binding compound is preferably present in an amount of 3 wt % or less of the phosphorus-binding compound, based on total dry matter intake of feed ration consumed by animal, more preferably 0.1-3 wt %, for example about 1-2 wt %.

The animal is a ruminant, for example, a cow, a sheep, a goat, or the like. In a preferred embodiment, the animal is a cow, for example a dairy cow or a beef cow. The animal is preferably a dairy cow. The feed composition is preferably formulated in a manner suitable for a cow.

EXAMPLES

Example 1: Method for Feeding an Al-Containing Product Utilizing Dietary P:Al Ratio To optimize the feeding rate of an Al-containing product (e.g., zeolite A), a dietary P:Al weight ratio was devised that achieves a desired reduction in blood phosphorus concentration. In the method, a P:Al ratio of 0.8:1 to 1.1:1 reduces blood P to about 1.8-3 mg/dL and requires three methodological steps: (1) dietary formulation and feeding to reach a dietary P:Al ratio of 0.8:1 to 1.1:1, (2) confirmatory tests of feed samples to validate and confirm optimal dietary P:Al ratio, and (3) analysis and confirmation of reduced blood P concentrations between 1.8-3 mg/dL in periparturient cows fed the Al-containing product, which has been optimized for a 0.8:1 to 1.1:1 dietary P:Al ratio.

Step 1. Dietary Formulation and Feeding

In order to achieve the end goal of restricting dietary and blood P, utilizing an Al-containing product, a dietary ratio of 0.8:1 to 1.1:1 P:Al (FIG. 2) was formulated and fed. In a prepartum dairy cow diet, the basal Al content is approximately 400 ppm on a dry matter basis, or a dietary P:Al ratio of 8:1 to 10:1, when grain, protein sources and silages are all mixed to form a totally mixed ration (TMR). Thus, in order to attain a dietary P:Al ratio of 0.8:1 to 1.1:1, an Al-containing product is supplemented into the TMR to increase the Al content and allow for the formation of the aluminum phosphate complex within the gastrointestinal tract of the animal to reduce available dietary P. Supplementation rate of an Al-containing product is fed in accordance with dietary P levels to reach the targeted range of dietary P:Al ratio mentioned previously (0.8:1 to 1.1:1). As dietary P content (wt %) increases, supplementation of Al is increased. Concordantly, as dietary P content (wt %) decreases, supplementation of an Al-containing product is decreased to maintain a dietary P:Al ratio of 0.8:1 to 1.1:1 based on ration feedstuffs.

Step 2. Dietary Confirmation

Variation in dietary P and Al levels can occur from ration formulation to feeding and placement in front of animals for multiple reasons, so confirmation of formulation and feeding is done to see if dietary 0.8:1 to 1.1:1 P:Al ratio is being met in the actual diet. To measure P and Al content in feed and thus determine dietary P:Al ratio, a minimum of 2 TMR samples were taken of feed being fed and presented to prepartum cows. Upon collection of TMR samples from the feed bunk or mixer wagon, feed samples were sent into a forage analysis laboratory to be analyzed for P and Al content via inductively coupled plasma (ICP) analysis. ICP analysis is an analytical technique that is able to identify and quantify the amount of P and Al within a sample based on the ionization of the elements in response to intense heating. The spectral emissions of the ionization are then quantified on a spectrometer which will translate into concentrations of specific elements. It is important that P and Al analysis is performed under ICP due to the larger linear range and thus assure accuracy of measurements.

Once analyzed, dietary P and Al content is available on a DM basis to calculate the dietary P:Al ratio and confirm if diet formulation is aligned with the actual feed mixture. If dietary P:Al is within the 0.8:1 to 1.1:1 ratio, then the methodology moves on to the blood P confirmation step. If dietary P:Al ratio is above target (greater than 1.1:1 dietary P:Al ratio), formulation adjustments were made. These adjustments may come through increasing the Al-containing product to decrease dietary P:Al ratio or decrease dietary P through feeding alternative forages or protein sources to decrease dietary P:Al ratio to fall within the 0.8:1 to 1.1:1 target. If dietary P:Al ratio is too low (less than 0.8:1 dietary P:Al ratio), then diet formulation was also adjusted. Decreasing the Al-containing product in formulation or increasing dietary P was done to increase the dietary P:Al ratio to fall between the desired 0.8:1 to 1.1:1 dietary P:Al ratio. Once formulation adjustments have occurred and feed samples have been re-sampled, re-analyzed and dietary P:Al ratio has been found to be between 0.8:1 to 1.1:1, the methodology moves forward to confirm proper blood P levels have been achieved.

Step 3. Blood Phosphorus Confirmation

A dietary P:Al ratio between 0.8:1 to 1.1:1, based on the data presented herein (FIG. 2), results in a blood P concentration of 1.8-3 mg/dL. To confirm that optimizing the dietary P:Al ratio resulted in a reduction in blood P to the aforementioned range, blood sampling of periparturient cows in the prepartum period and/or in the immediate time around calving was conducted as follows.

Prepartum Blood Sampling

A minimum of ten prepartum dairy cows were blood sampled after consuming the diet that was supplemented with an Al-containing product (zeolite A) to reach a dietary P:Al based ratio of 0.8:1 to 1.1:1. Cows consumed the TMR supplemented with the Al-containing product for a minimum of 7 days prior to being eligible for blood sampling. Blood samples were collected from the coccygeal vessel in the tailhead and then analyzed for blood P concentrations.

Postpartum Cow Blood Sampling

A minimum of ten dairy cows were blood sampled within 6-12 hours of calving after consuming the diet supplemented with the Al-containing product that was formulated and analyzed to reach 0.8:1 to 1.1:1 dietary P:Al ratio. Cows consumed the TMR for a minimum of 7 days to be eligible for blood sampling. Blood samples were collected from the coccygeal vessel in the tailhead and then analyzed for blood P concentrations.

Based on a dietary P:Al ratio of 0.8:1 to 1.1:1, prepartum and the postpartum dairy cows had blood P concentrations in a range of 1.8-3 mg/dL. If blood P values became less than 1.8 mg/dL, re-sampling of total mixed ration (TMR) was done, and dietary confirmation done again as dietary P:Al ratio is less than 0.8:1 and needed to be re-formulated. If blood P concentrations were above 3 mg/dL, then re-sampling of TMR was done to confirm dietary P:Al ratio as a dietary P:Al ratio of greater than 1.1:1 required re-formulation to target the 0.8:1 to 1.1:1 dietary P:Al ratio.

The methods as defined above were conducted on 15 dairy farms feeding zeolite A to prepartum dairy cows and data is shown in FIG. 2. Additional Zeolite literature is shown in Table 1. Table 1 provides blood Ca and P responses to feeding zeolite A, an aluminum-based product, to periparturient dairy cows. Due to different and multiple data points both pre- and post-calving, a singular blood Ca and P measurement nearest to calving is represented with responses to feeding zeolite A expressed as percentage of the comparative treatment.

TABLE 1

| Reference | Treatments | Dietary Ca % DM Zeolite | Dietary Ca % DM Control | Dietary P % DM Zeolite | Dietary P % DM Control | Blood Ca Response % of Control Zeolite vs Control | Blood P Response % of Control Zeolite vs Control | Clinical Milk Fever % of Control Zeolite vs Control |
|---|---|---|---|---|---|---|---|---|
| Thilsing-Hansen et al., 2001 | Zeolite vs Control | 0.64 | 0.45 | 0.64 | 0.45 | +27% | NR | −33% |
| Kerwin et al., 2019 | Zeolite vs Control | 0.65 | 0.68 | 0.38 | 0.39 | +22% | −50% | 0% |
| Frizzarini et al., 2022 | Zeolite vs DCAD | NR | NR | NR | NR | +11% | −47% | NR |
|  | Zeolite vs Control | NR | NR | NR | NR | +17% | −49% | NR |
| Crookenden et al., 2020 | Zeolite vs Control | NR | NR | NR | NR | +13% | −73% | NR |
| Pallesen et al., 2007 | Zeolite vs Control | 0.61 | 0.69 | 0.61 | 0.69 | +33% | −10% | −75% |
|  | Zeolite vs Control | 0.61 | 0.33 | 0.61 | 0.69 | +57% | −72% | −100% |
| Grabherr et al., 2008 | Zeolite vs Control | 0.42 | 0.38 | 0.42 | 0.38 | +11% | −22% | NR |
| Saraiva de Oliveira, 2021 | Zeolite vs DCAD | 0.57 | 2.53 | 0.36 | 0.43 | +13% | −45% | −51% |
| Thilsing-Hansen et al., 2002 | Zeolite vs Control | 0.60 | 0.60 | 0.30 | 0.30 | +12% | −36% | 0% |
| Khachouf et al., 2019 | Zeolite vs Control | 2.79 | 2.79 | 0.80 | 0.80 | +8% | 0% | NR |

NR = not reported

The data demonstrates the efficacy of the method as blood P levels are highly predictable based on the P:Al ratio fed. The data also supports feeding prepartum cows a dietary P:Al ratio of 0.8:1 to 1.1:1 to achieve periparturient blood P levels of 1.8-3.3 mg/dL.

CONCLUSION

Collectively, an Al-containing product, such as zeolite A, improves calcium homeostasis and blood calcium levels in the periparturient cow through manipulating P homeostasis and inducing a mild hypophosphatemia. The methodology herein demonstrates a process to induce a transient phase hypophosphatemia in periparturient dairy cattle through manipulating the dietary P:Al ratio while feeding an Al-containing product to target a dietary P:Al ratio of 0.8:to 1.1:1 which has been shown to result in desired blood P concentrations of 1.8-3 mg/dL in periparturient dairy cows.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended features should not be limited to the description of preferred embodiments contained in this disclosure. All references cited herein are incorporated by reference in their entirety.

What is claimed is:

1. A method of reducing risk of periparturient hypocalcemia in at least one periparturient ruminant animal, the method comprising the steps of:
   a) measuring a blood phosphorus (P) concentration in the at least one periparturient ruminant animal; and
   b) perorally administering to the periparturient ruminant animal during at least part of a prepartum period of the periparturient ruminant animal a composition comprising:
   i) an aluminum-based phosphorus-binding compound present in an amount sufficient to provide aluminum at a concentration of 0.2-0.75% Alu by weight of the total dry matter in the feed ration consumed by the animal, wherein the phosphorus-binding compound is selected from the group consisting of synthetic zeolites, aluminum sulfate, aluminum chloride, aluminum hydroxide, a hydrate thereof, and any mixture thereof; and
   ii) a pharmacologically acceptable carrier comprising one or more animal feed components other than the phosphorus-binding compound;
   wherein the feed composition provides a dietary phosphorus (P) to aluminum (Al) weight ratio in a range of 0.8:1 to 1.1:1 to control blood phosphorus concentration in the periparturient ruminant animal in a range of 2.0-3.0 mg P per dL of blood;
   wherein the phosphorus-binding compound reduces bioavailability of phosphorus in a digestive system of the periparturient ruminant animal;
   wherein the periparturient ruminant animal is a dairy cow; and
   wherein step a) can be performed before or after step b).

2. The method of claim 1, wherein:
   if the blood phosphorus concentration is below the range, administration rate of the composition of step b) is decreased or the composition is reformulated to decrease the amount of the compound and/or increase the phosphorus to aluminum ratio; and,
   if the blood phosphorus concentration is above the range, administration rate of the composition of step b) is increased or the composition is reformulated to increase the amount of the compound relative to phosphorus in the composition and/or decrease the phosphorus to aluminum ratio,
   so that the blood phosphorus concentration is brought into the range.

3. The method of claim 1, wherein the measuring of step a) is done periodically.

4. The method of claim 1, wherein the phosphorus-binding compound of step b) reduces bioavailability of the phosphorus in a digestive system of the periparturient ruminant animal.

5. A composition for reducing risk of periparturient hypocalcemia in a periparturient ruminant animal, the composition comprising:
   a) an aluminum-based phosphorus-binding compound present in an amount sufficient to provide aluminum at a concentration of 0.2-0.75% Alu by weight of the total dry matter in the feed ration consumed by the animal, wherein the phosphorus-binding compound is selected from the group consisting of synthetic zeolites, aluminum sulfate, aluminum chloride, aluminum hydroxide, a hydrate thereof, and any mixture thereof; and
b) a pharmacologically acceptable carrier comprising one or more animal feed components other than the phosphorus-binding compound;
wherein the feed composition provides a dietary phosphorus (P) to aluminum (Al) weight ratio in a range of 0.8:1 to 1.1:1 to control blood phosphorus concentration in the periparturient ruminant animal in a range of 2.0-3.0 mg P per dL of blood;
wherein the phosphorus-binding compound reduces bioavailability of phosphorus in a digestive system of the periparturient ruminant animal; and
wherein the periparturient ruminant animal is a dairy cow.

6. The composition of claim 5, wherein the feed composition is suitable for a dairy cow.

* * * * *